(12) United States Patent
Kuwabara (10) Patent No.: US 8,311,771 B2
(45) Date of Patent: Nov. 13, 2012

(54) INSPECTION METHOD OF SOI WAFER

(75) Inventor: Susumu Kuwabara, Annaka (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 0 days.

(21) Appl. No.: 13/262,050

(22) PCT Filed: Apr. 5, 2010

(86) PCT No.: PCT/JP2010/002469
§ 371 (c)(1),
(2), (4) Date: Sep. 29, 2011

(87) PCT Pub. No.: WO2010/125747
PCT Pub. Date: Nov. 4, 2010

(65) Prior Publication Data
US 2012/0035863 A1 Feb. 9, 2012

(30) Foreign Application Priority Data

May 1, 2009 (JP) .................................. 2009-111785

(51) Int. Cl.
*G01B 11/02* (2006.01)
*G02F 1/00* (2006.01)
*G06F 19/00* (2011.01)
*G06F 17/40* (2006.01)
*H05K 13/08* (2006.01)

(52) U.S. Cl. ..................... 702/172; 73/865.8; 356/237.4; 356/237.5; 356/600; 356/630; 382/108; 382/149; 438/14; 438/16; 702/40; 702/189

(58) Field of Classification Search .................. 73/732.1, 73/865.8; 356/237.1, 237.2, 137.3, 237.4, 356/237.5, 600, 601, 625, 630; 382/100, 382/108, 141, 145, 149; 438/14, 16; 700/90, 700/95, 108, 109, 110, 117, 121; 702/1, 702/33, 35, 36, 40, 127, 155, 170, 172, 187, 702/189; 708/100, 105, 200

See application file for complete search history.

(56) References Cited

U.S. PATENT DOCUMENTS 3,063,867 A * 11/1962 Emery, Jr. ...................... 427/10
(Continued)

FOREIGN PATENT DOCUMENTS

JP        10-293101 A   *  11/1988
(Continued)

OTHER PUBLICATIONS

International Search Report issued in International Application No. PCT/JP2010/002469 on Apr. 27, 2010 (with translation).

*Primary Examiner* — Edward Cosimano
(74) *Attorney, Agent, or Firm* — Oliff & Berridge, PLC (57) ABSTRACT

An inspection method of an SOI wafer in which profiles P1 and P2 are calculated in the SOI wafer to be inspected and in an SOI wafer having a film thickness of the SOI layer thicker or thinner than that of the SOI wafer to be inspected, respectively; a profile P3 of a difference between P1 and P2, or a profile P4 of a change ratio of P1 and P2 is calculated; light having the wavelength band selected on the basis of a maximum peak wavelength within the calculated profiles P3 or P4 is irradiated to the surface of the SOI wafer to be inspected, to detect the reflected-light from the SOI wafer; and a place of a peak generated by an increase in reflection intensity of the detected reflected-light is found, as the defect caused by the change in the film thickness of the SOI layer.

18 Claims, 11 Drawing Sheets

U.S. PATENT DOCUMENTS

| | | | |
|---|---|---|---|
| 3,099,579 A * | 7/1963 | Spitzer et al. | 117/86 |
| 3,396,627 A * | 8/1968 | Rouy et al. | 356/446 |
| 3,427,109 A * | 2/1969 | Beattie et al. | 356/237.2 |
| 3,518,133 A * | 6/1970 | Glendinning | 438/14 |
| 5,376,215 A | 12/1994 | Ohta et al. | |
| 5,835,225 A * | 11/1998 | Thakur | 356/630 |
| 6,654,129 B1 * | 11/2003 | Uda et al. | 356/504 |
| 2002/0173084 A1 | 11/2002 | Ohkawa | |
| 2004/0130718 A1 | 7/2004 | Krishnan | |
| 2010/0007872 A1 | 1/2010 | Isozaki et al. | |

FOREIGN PATENT DOCUMENTS

| | | |
|---|---|---|
| JP | A-4-328844 | 11/1992 |
| JP | 11-23483 A * | 1/1999 |
| JP | A-2002-343842 | 11/2002 |
| JP | A-2004-132755 | 4/2004 |
| JP | A-2006-112871 | 4/2006 |
| JP | A-2006-524828 | 11/2006 |
| JP | A-2008-218799 | 9/2008 |
| WO | WO 2004/076969 A1 | 9/2004 |

* cited by examiner

INSPECTION METHOD OF SOI WAFER

TECHNICAL FIELD

The present invention relates to inspection of a semiconductor substrate having a multilayer film structure such as an SOI wafer, or to an inspection technology in a device process using the substrate, and particularly to a detection technology of various surface defects and pattern defects by detecting reflected-light in inspection using light.

BACKGROUND ART

In a manufacture process of a semiconductor substrate having a multilayer film structure and a device process using the substrate, it is important to detect various defects on a surface and in the close vicinity of the surface, which affect a device yield, upon process management and improvement of the yield. In recent years, SOI wafers are used for device fabrication as the semiconductor substrate having a multilayer film structure, and processes are thereby complex. As devices have become finer, the importance of optical inspection has been increased from the viewpoint of inspection capability or throughput.

Examples of the above-described defects to be an inspection object on the surface and in the close vicinity of the surface include crystal defects, extraneous substances, scratches, pattern defects, and deposited abnormal patterns. A dark-field inspection method using scattered light or a bright-field inspection method using a microscope is used to detect the defects.

For example, there are disclosed an inspection method of a semiconductor substrate by detecting the scattered light when laser light is irradiated to the semiconductor substrate (See Patent Literature 1), and a surface inspection method for an inspection subject, where two or more kinds of laser are switched or mixed to make the laser incident on the inspection subject by a same incident angle (See Patent Literature 2).

CITATION LIST

Patent Literature

Patent Literature 1: Japanese Unexamined Patent publication (Kokai) No. 2006-112871
Patent Literature 2: Japanese Unexamined Patent publication (Kokai) No. 2004-132755

SUMMARY OF INVENTION

One specific example of the above-described defects is a defect caused by a change in the film thickness of an SOI layer (a defect accompanied by the change in the film thickness), and this affects characteristics of devices to be fabricated on the SOI. It is therefore important to inspect the defect caused by the change in the film thickness of the SOI layer at high sensitivity during a manufacture process of the SOI wafer or the inspection of an SOI wafer product.

One of the defects caused by the change in the film thickness of the SOI layer is in the form of a hollow due to the decrease in the film thickness of the SOI layer. The depth thereof does not reach a buried insulator layer (a BOX layer), and the depth is between approximately 10 nm and a depth that does not reach the insulator layer. The size thereof has a larger extent than a wavelength that is used in the laser scattering method.

The extent of this defect is typically observed to be approximately 10 µm. The defect having an extent between approximately 1 to 2 µm and several hundred µm can be observed by adjusting the magnification of a microscope of an optical inspection apparatus. With respect to a shape thereof, there is possibility to detect a circular shape, a shape obtained by connecting circles, and an elliptic shape, and further an angled shape such as a rectangle in a device process. Moreover, there may be exist a defect having a mound shape in which the layer becomes thick due to the increase in the film thickness of the SOI layer, which is not the above-described hollow shape due to the decrease in the film thickness of the SOI layer.

It is difficult to inspect the defects caused by the changes due to the increase and decrease in the film thickness of the SOI layer at high sensitivity by a conventional inspection method. For example, the above-described conventional method using the laser scattering is useful for detecting an extraneous substance such as particle, but scattering intensity in this method is so weak that detection sensitivity is not sufficient with respect to the defects caused by the change in the film thickness on a micro area of the SOI layer. In addition, it is difficult to detect the defects caused by the change in the film thickness separately from the extraneous substance and the like.

The present invention was accomplished in view of the above-explained problems, and its object is to provide an inspection method of an SOI wafer that enables the inspection of the defects caused by the change in the film thickness of the SOI layer of the SOI wafer at high sensitivity and at low cost, without influence of the extraneous substance on the surface of the SOI wafer.

To achieve this object, the present invention provides an inspection method of an SOI wafer including, using an optical inspection apparatus having a light source for irradiating light having a wavelength band of a visible light wavelength or more to irradiate the light from the light source to a surface of the SOI wafer having an SOI layer formed on a buried insulator layer, and detecting reflected-light from the SOI wafer to find defects caused by changes due to an increase and a decrease in a film thickness of the SOI layer on the surface of the SOI wafer, the method comprising at least the steps of: calculating a profile P1 showing wavelength dependency of reflectance with respect to the light having a wavelength band of a visible light wavelength or more, in the SOI wafer to be inspected; calculating a profile P2 showing wavelength dependency of reflectance with respect to the light having a wavelength band of a visible light wavelength or more, in an SOI wafer having a film thickness of the SOI layer thicker or thinner than that of the SOI wafer to be inspected by a predetermined thickness t [nm]; calculating a profile P3 (=P2−P1) of a difference between the calculated profiles P1 and P2, or a profile P4 (=(P2−P1)/P1) of a change ratio of the calculated profiles P1 and P2, to select a wavelength λ or a wavelength band in close vicinity of a maximum peak wavelength $\lambda_M$ within the calculated profiles P3 or P4; irradiating light having the selected wavelength λ or wavelength band to the surface of the SOI wafer to be inspected, to detect the reflected-light from the SOI wafer; and finding a place of a peak generated by an increase in reflection intensity of the detected reflected-light, as the defect caused by the change in the film thickness of the SOI layer on the surface of the SOI wafer.

In this manner, when the method has the steps of calculating a profile P1 showing wavelength dependency of reflectance with respect to the light having a wavelength band of a visible light wavelength or more, in the SOI wafer to be inspected; calculating a profile P2 showing wavelength dependency of reflectance with respect to the light having a wavelength band of a visible light wavelength or more, in an SOI wafer having a film thickness of the SOI layer thicker or thinner than that of the SOI wafer to be inspected by a predetermined thickness t [nm]; calculating a profile P3 (=P2−P1) of a difference between the calculated profiles P1 and P2, or a profile P4 (=(P2−P1)/P1) of a change ratio of the calculated profiles P1 and P2, to select a wavelength λ or a wavelength band in close vicinity of a maximum peak wavelength $\lambda_M$ within the calculated profiles P3 or P4; irradiating light having the selected wavelength λ or wavelength band to the surface of the SOI wafer to be inspected, to detect the reflected-light from the SOI wafer; and finding a place of a peak generated by an increase in reflection intensity of the detected reflected-light, as the defect caused by the change in the film thickness of the SOI layer on the surface of the SOI wafer, the defects caused by the change in the film thickness of the SOI layer on the SOI wafer surface can be found at high sensitivity and at low cost, without influence of noise due to the extraneous substance present on the surface of the SOI layer. In addition to this, only the defects caused by the change in the film thickness of the SOI layer can be selectively detected.

In this case, the profile P2 can be calculated in the step of calculating the profile P2 as follows. In case of finding the defects caused by the change due to the decrease in the film thickness of the SOI layer, the profile P2 of the SOI wafer having a film thickness of the SOI layer thinner by a thickness t is calculated, and in case of finding the defects caused by the change due to the increase in the film thickness of the SOI layer, the profile P2 of the SOI wafer having a film thickness of the SOI layer thicker by a thickness t is calculated.

When the profile P2 is calculated in the step of calculating the profile P2 in such a manner that, in case of finding the defects caused by the change due to the decrease in the film thickness of the SOI layer, the profile P2 of the SOI wafer having a film thickness of the SOI layer thinner by a thickness t is calculated, and in case of finding the defects caused by the change due to the increase in the film thickness of the SOI layer, the profile P2 of the SOI wafer having a film thickness of the SOI layer thicker by a thickness t is calculated, the inspection can be performed by selecting the wavelength or wavelength band suitable for each of the defects caused by the change due to the increase and the change due to the decrease in the film thickness of the SOI layer. As a result, the defects can be found more surely at high sensitivity, and the defects caused by the change due to the increase and decrease can be separately found.

In this case, a threshold value of the reflection intensity of the detected reflected-light can be set, and the defects having the reflection intensity equal to or more than the threshold value can be selectively found.

In this manner, when the threshold value of the reflection intensity of the detected reflected-light is set, and the defects having the reflection intensity equal to or more than the threshold value are found, only the defects that are caused by the change in the film thickness of the SOI layer and that affect a device process can be selectively found.

In this case, the predetermined thickness t is preferably set on the basis of film thickness uniformity of the SOI wafer to be inspected.

In this manner, when the predetermined thickness t is set on the basis of film thickness uniformity of the SOI wafer to be inspected, the inspection can be performed by selecting appropriate wavelength or wavelength band on the basis of the film thickness uniformity, the influence of noise due to an nonuniform film thickness on the inspection can be suppressed, and the defects caused by the change in the film thickness of the SOI layer can be thereby found more surely at high sensitivity.

In this case, the predetermined thickness t can be set in a range of 5 to 20 nm.

In this manner, when the predetermined thickness t is set in a range of 5 to 20 nm, the wavelength or wavelength band suitable for an SOI wafer having a film thickness uniformity of ±3 nm or less can be selected to inspect at high sensitivity. Therefore, the method of the present invention can be preferably used for the SOI wafer having a film thickness uniformity of ±3 nm or less, manufactured by the ion implantation delamination method.

Moreover, in case of calculating the profile P2 of the SOI wafer having a film thickness of the SOI layer thinner by the predetermined thickness t in the step of calculating the profile P2, the wavelength λ or wavelength band can be selected in a range of $\lambda_M-20$ [nm] to $\lambda_M+100$ [nm], and in case of calculating the profile P2 of the SOI wafer having a film thickness of the SOI layer thicker by the predetermined thickness t in the step of calculating the profile P2, the wavelength λ or wavelength band can be selected in a range of $\lambda_M-100$ [nm] to $\lambda_M+20$ [nm].

When the wavelength or wavelength band is selected in the step of calculating the profile P2 in such a manner that, in case of calculating the profile P2 of the SOI wafer having a film thickness of the SOI layer thinner by the predetermined thickness t, the wavelength λ or wavelength band is selected in a range of $\lambda_M-20$ [nm] to $\lambda_M+100$ [nm], and in case of calculating the profile P2 of the SOI wafer having a film thickness of the SOI layer thicker by the predetermined thickness t, the wavelength λ or wavelength band is selected in a range of $\lambda_M-100$ [nm] to $\lambda_M+20$ [nm], it is possible to select the wavelength λ or wavelength band that enables the inspection to be performed more surely at high sensitivity according to the profile P2.

The inspection method of an SOI wafer according to the present invention, including finding the defects caused by the changes due to the increase and the decrease in the film thickness of the SOI layer on the surface of the SOI wafer, has at least the steps of: calculating a profile P1 showing wavelength dependency of reflectance with respect to the light having a wavelength band of a visible light wavelength or more, in the SOI wafer to be inspected; calculating a profile P2 showing wavelength dependency of reflectance with respect to the light having a wavelength band of a visible light wavelength or more, in an SOI wafer having a film thickness of the SOI layer thicker or thinner than that of the SOI wafer to be inspected by a predetermined thickness t [nm]; calculating a profile P3 (=P2−P1) of a difference between the calculated profiles P1 and P2, or a profile P4 (=(P2−P1)/P1) of a change ratio of the calculated profiles P1 and P2, to select a wavelength λ or a wavelength band in close vicinity of a maximum peak wavelength $\lambda_M$ within the calculated profiles P3 or P4; irradiating light having the selected wavelength λ or wavelength band to the surface of the SOI wafer to be inspected, to detect the reflected-light from the SOI wafer; and finding a place of a peak generated by an increase in reflection intensity of the detected reflected-light, as the defect caused by the change in the film thickness of the SOI layer on the surface of the SOI wafer. The defects caused by the change in the film thickness of the SOI layer on the SOI wafer surface can be thereby found at high sensitivity and at low cost, without the influence of noise due to the extraneous substance present on the surface of the SOI layer. In addition to this, only the defects caused by the change in the film thickness of the SOI layer can be selectively detected.

DESCRIPTION OF EMBODIMENTS

Hereinafter, the embodiment of the present invention will be explained, but the present invention is not restricted thereto.

In recent years, SOI wafers are used for device fabrication as a semiconductor substrate having a multilayer film structure, and processes are thereby complex. As devices have become finer, the importance of optical inspection has been increased from the viewpoint of inspection capability or throughput.

One of the objects of the above-described optical inspection is the defect caused by the change in the film thickness of the SOI layer. It is important to inspect the defect caused by the change in the film thickness of the SOI layer at high sensitivity during a manufacture process of the SOI wafer or the inspection of an SOI wafer product.

It is difficult to inspect the defects caused by the change in the film thickness of the SOI layer at high sensitivity by a conventional inspection method. For example, the above-described conventional method using the laser scattering is useful for detecting an extraneous substance such as particle, but scattering intensity in this method is so weak that detection sensitivity is not sufficient with respect to the defects caused by the change in the film thickness on a micro area of the SOI layer. In addition, it is difficult to detect the defects caused by the change in the film thickness separately from the extraneous substance and the like.

In view of this, the present inventor repeatedly keenly conducted studies to solve the problems. As a result, the present inventor conceived that, in the bright-field inspection method using visible light, which is low-cost, the inspection is performed by using inspection light having a wavelength band in which the change in reflectance is increased by the change in the film thickness of the SOI layer, and thereby the defects caused by the change in the film thickness of the SOI layer or an area where the film thickness is abnormal can be found at high sensitivity.

Moreover, the present inventor also conceived as follows. The difference or change ratio between the profile showing wavelength dependency of reflectance with respect to visible light in the SOI wafer to be inspected having a film thickness of the SOI layer and that profile in an SOI wafer having the film thickness that differs by a predetermined thickness from the film thickness of the SOI layer of the SOI wafer to be inspected is calculated. The inspection is performed by using light having a wavelength or a wavelength band in close vicinity of the wavelength showing the maximum peak at which the difference or change ratio is increased. The change in contrast of the reflected-light can be stressed which is caused by changing the film thickness of the SOI layer by a predetermined thickness, and the defects caused by the change in the film thickness of the SOI layer can be thereby found at high sensitivity and at low cost. Thereby, the present inventor brought the present invention to completion.

In the inspection method of an SOI wafer according to the present invention, the optical inspection apparatus having the light source for irradiating light having a wavelength band of a visible light wavelength or more is used to inspect. As described above, the inspection method of an SOI wafer according to the present invention is a low-cost inspection method, since the visible light, which is low-cost, is used to inspect.

Moreover, the defects to be inspected by the inspection method of an SOI wafer according to the present invention are the defects caused by the change in the film thickness of the SOI layer. The defects are classified into the defect generated by making a part of the layer thinner by the change due to the decrease in the film thickness of the SOI layer, such as the defect having a hollow shape, and the defect generated by making a part of the layer thicker by the change due to the increase in the film thickness of the SOI layer, such as the defect having a mound shape.

Figure 1:
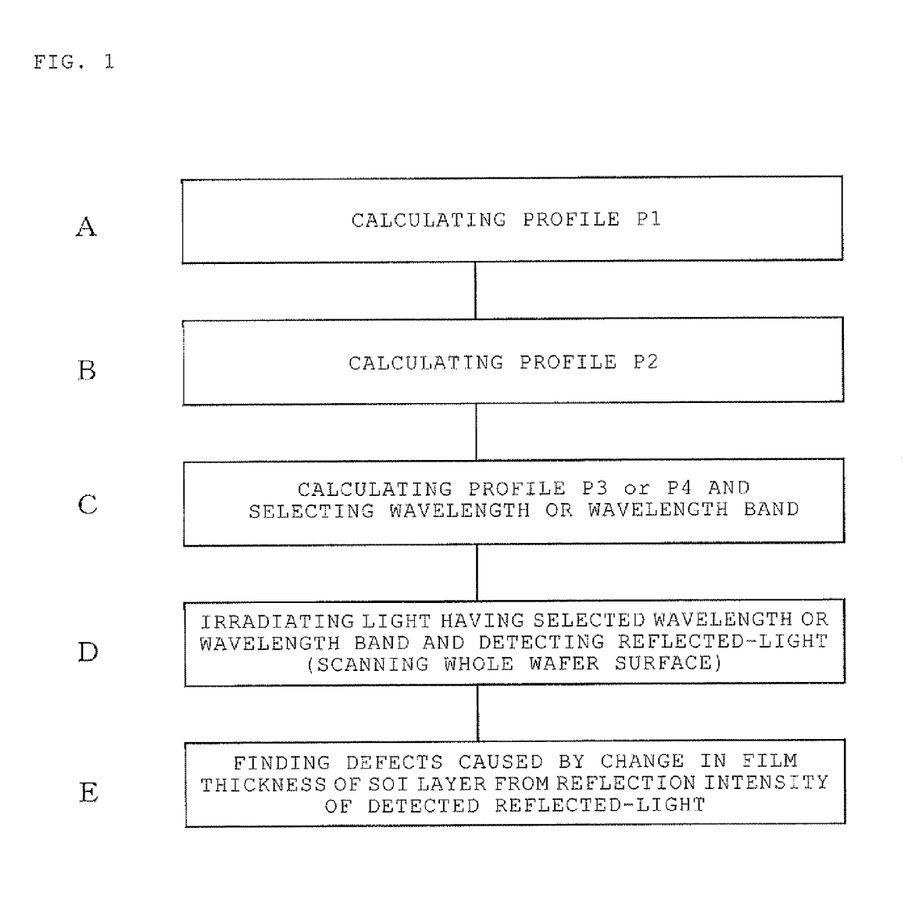
FIG. 1 is a flowchart showing the steps of the inspection method of an SOI wafer of the present invention.

FIG. 1 is a flowchart showing the steps of the inspection method of an SOI wafer of the present invention.

An object to be inspected of the inspection method of an SOI wafer according to the present invention is the SOI wafer having the SOI layer formed on the buried insulator layer (the BOX layer). Here, the film thickness of the SOI layer is S [nm], and the thickness of the buried insulator layer (the BOX layer) is B [nm].

First, the profile P1 showing the wavelength dependency of reflectance with respect to the light having a wavelength band of a visible light wavelength or more is calculated by simulation, in the SOI wafer to be inspected (See A in FIG. 1).

Next, the profile P2 showing the wavelength dependency of reflectance with respect to the light having a wavelength band of a visible light wavelength or more is calculated by simulation, in an SOI wafer having a film thickness of the SOI layer thicker or thinner than that of the SOI wafer to be inspected by a predetermined thickness t [nm] (See B in FIG. 1).

Figure 2:
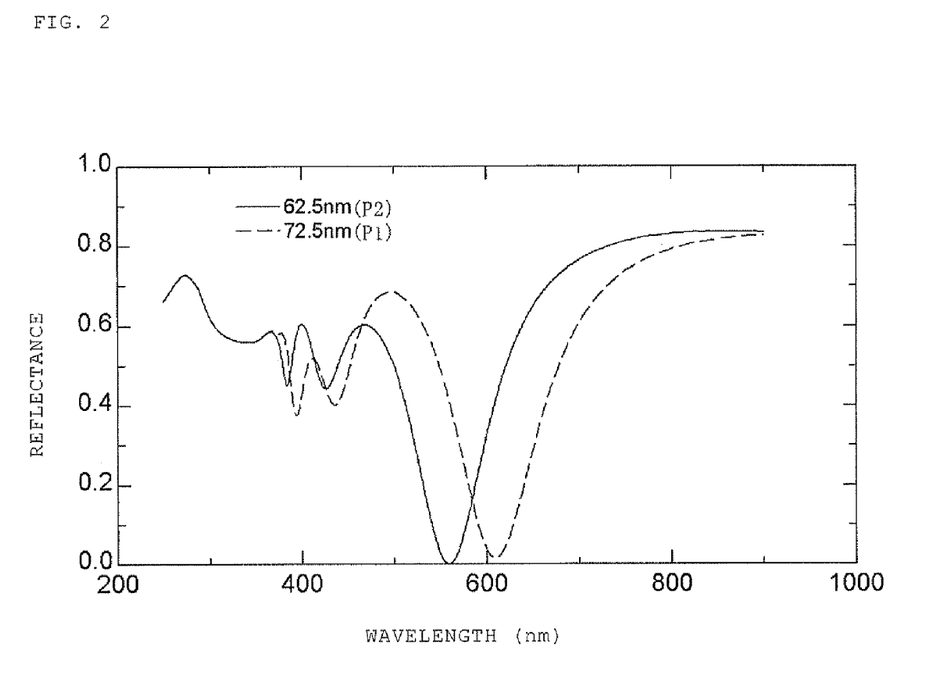
FIG. 2 is a graph showing an example of the calculated profiles P1 and P2.

FIG. 2 shows an example of the profile 21 in the event that the film thickness S of the SOI layer of the SOI wafer to be inspected is 72.5 nm and the thickness B of the buried insulator layer thereof is 145 nm, and an example of the profile P2 in the event that an SOI wafer having a film thickness of the SOI layer thinner than that of the SOI wafer to be inspected by approximately 10 nm is hypothesized, that is, in the event that the predetermined thickness t is 10 nm and hence the film thickness of the SOI layer of the hypothetical SOI wafer is 62.5 nm. As shown in FIG. 2, it is understood that the profiles P1 and P2 showing the wavelength dependency of reflectance are varied by changing the thickness of the SOI layer.

Next, the profile P3 (=P2−P1) of the difference between the profiles P1 and P2 calculated by simulation, or the profile P4 (=(P2−P1)/P1) of the change ratio of the calculated profiles P1 and P2 is calculated. The wavelength λ or the wavelength band in close vicinity of the maximum peak wavelength $λ_M$ among increasing peaks within the calculated profiles P3 or P4 is thereafter selected as the wavelength λ or the wavelength band of light that is to be used for irradiating to the surface of the SOI wafer in a subsequent step (See C in FIG. 1). Hereinafter, a specific example will be explained.

Figure 3:
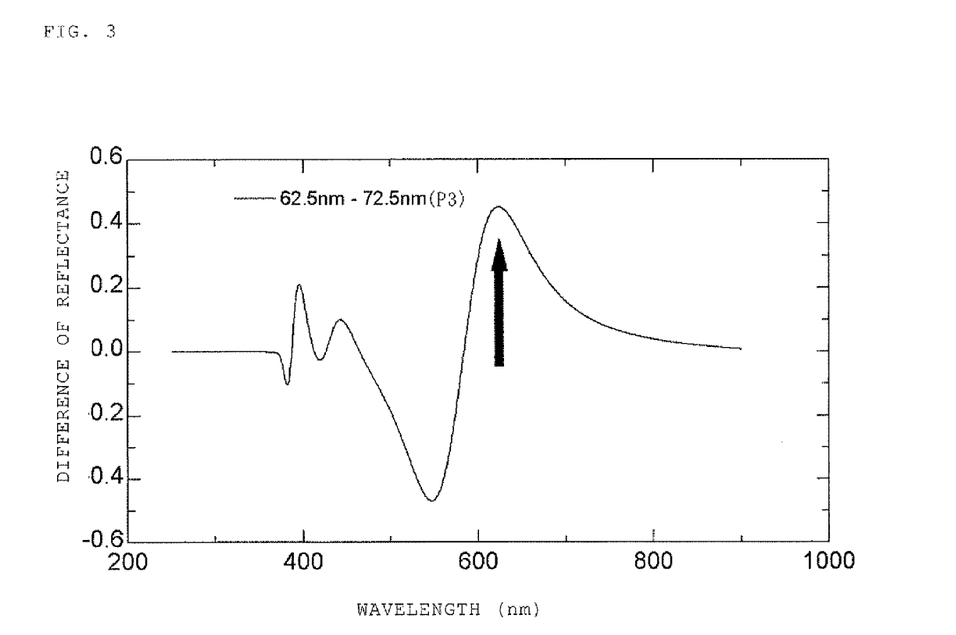
FIG. 3 is a graph showing an example of the calculated profile P3.

FIG. 3 is a graph showing the calculated profile P3 of the difference between the profiles P1 and P2 shown in FIG. 2. As shown in FIG. 3, some places showing the increasing peaks (upward peaks) are observed in the profile P3. The place shown by an arrow among them is the maximum peak wavelength $λ_M$ (approximately 620 nm). The wavelength λ or the wavelength band in close vicinity of the maximum peak wavelength $λ_M$ is selected as an inspection wavelength.

In this case, with regard to the wavelength λ or the wavelength band to be selected, the maximum peak wavelength $λ_M$ of the profile P3 may be selected as a single wavelength λ, or a single wavelength λ may be selected from a wavelength range in the close vicinity thereof. Alternatively, the close vicinity of the maximum peak wavelength $λ_M$ may be selected as a wavelength band.

In this case, the threshold value of the profile P3 or the profile P4 can be set. When the defects caused by the change in the film thickness of the SOI layer are selectively found only in the event that the profile is equal to or more than the threshold value, only the defects that are caused by the change in the film thickness of the SOI layer and that affect a device process can be detected.

Next, the optical inspection apparatus having the light source for irradiating light having the wavelength λ or wavelength band selected in a previous step is used to inspect the SOI wafer.

Here, the optical inspection apparatus used in the present invention is not restricted in particular as long as it has the light source for irradiating light having a wavelength band of a visible light wavelength or more and it can irradiate the light having the wavelength λ or wavelength band selected in a previous step to the SOI wafer to be inspected to detect the reflected-light thereof. For example, as shown in FIG. 4, the optical inspection apparatus 2 can be used which has a structure that a bandpass filter 4 is attached in front of a detection camera 5.

Figure 4:
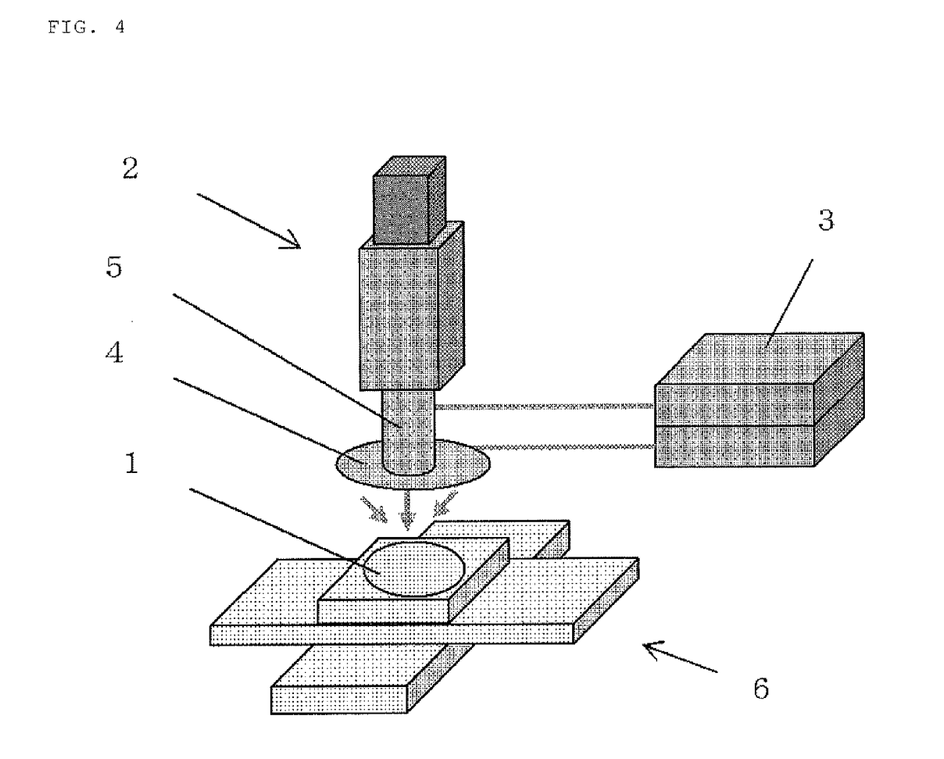
FIG. 4 is a schematic view showing an optical inspection apparatus that can be used in the inspection method of an SOI wafer of the present invention.

The optical inspection apparatus 2 shown in FIG. 4 can irradiate light to the surface of the SOI wafer 1 after filtering the light from the light source 3 by the bandpass filter 4 so as to carry only the light having a predetermined wavelength λ or wavelength band.

Alternatively, for example, an acoustic filter, a liquid crystal filter, or a wavelength-variable laser can be used to filter the light to be irradiated, instead of the bandpass filter 4.

Moreover, the wavelength λ can be set by the light source, and various lasers (an LD, gas laser, solid laser, and wavelength-variable laser), a light-emitting diode (LED), and a liquid crystal display (LCD) can be also used. Moreover, one signal of RGB signals of a color camera can be simply used.

With the above-described optical inspection apparatus 2, the light having the wavelength λ or wavelength band selected in a previous step is irradiated to the surface of the SOI wafer 1 to be inspected, and the reflected-light from the SOI wafer 1 is detected (See D in FIG. 1). In this case, the reflected-light is detected by scanning the whole surface of the SOI wafer with an XY axis stage 6 or an Rθ stage.

The place of the peak generated by the increase in reflection intensity of the detected reflected-light is found as the defect caused by the change in the film thickness of the SOI layer on the surface of the SOI wafer (See E in FIG. 1). Specifically, an image of the reflection intensity of the detected reflected-light is obtained, and the place on the image where the reflection intensity is increased to form the peak (the upward peak) can be extracted as the defect caused by the change in the film thickness of the SOI layer.

Figure 5:
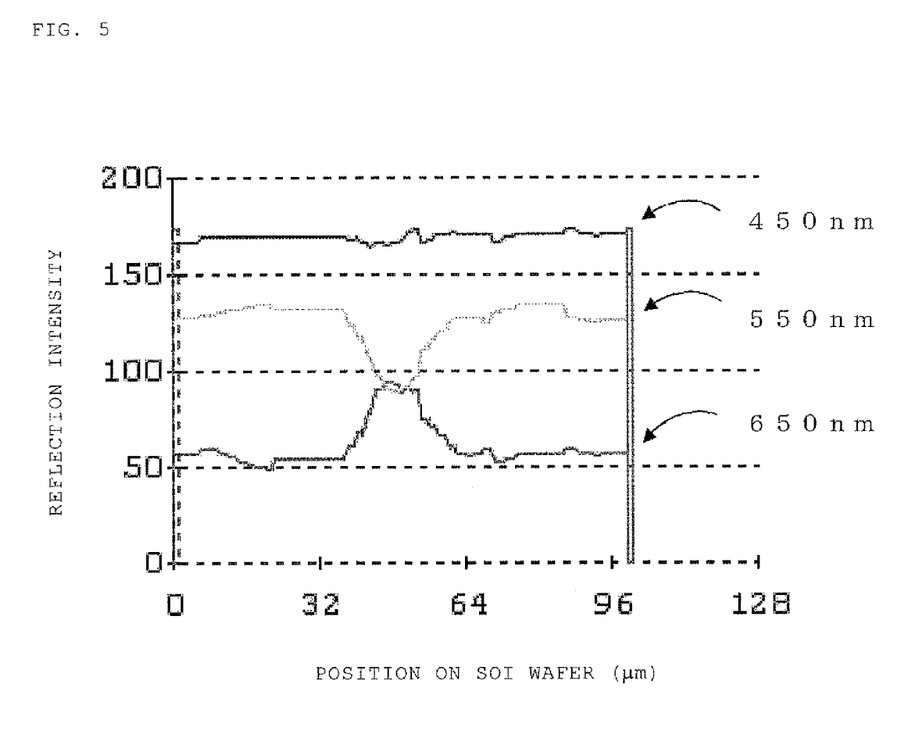
FIG. 5 is a graph showing an example of the reflection intensity of the detected reflected-light.

FIG. 5 shows the result of experiment in which the reflection intensity of the detected reflected-light was measured when three types of light each having one of three wavelengths (450 nm, 550 nm, and 650 nm) were irradiated to an area of the SOI wafer having an SOI layer film thickness S of 72.5 nm and a buried insulator layer thickness of 145 nm, and the defects caused by the change in the film thickness of the SOI layer were actually present.

FIG. 3 shows the result of calculating the profile P3 of this SOI wafer. The wavelength in the close vicinity of the maximum peak wavelength $λ_M$ (620 nm) calculated from FIG. 3 is a wavelength of 650 nm. As shown in FIG. 5, in case of a wavelength of 650 nm, the place where the reflection intensity of the detected reflected-light is the upward peak is located at a position of approximately 50 μm on the wafer, and the place is thus found as the defect caused by the change in the film thickness of the SOI layer. The actual defect caused by the change in the film thickness of the SOI layer is located at a position of approximately 50 μm on the wafer.

On the other hand, in case of a wavelength of 450 nm, there is no peak. In case of a wavelength of 550 nm, there is a place of a peak generated by the decrease (a downward peak).

As described above, the place of the peak generated by the increase in reflection intensity is observed at the position of the defect caused by the change in the film thickness of the SOI layer by using the inspection light having a wavelength in the close vicinity of $λ_M$, and the place is thus found as the defect caused by the change in the film thickness of the SOI layer.

Figure 6:
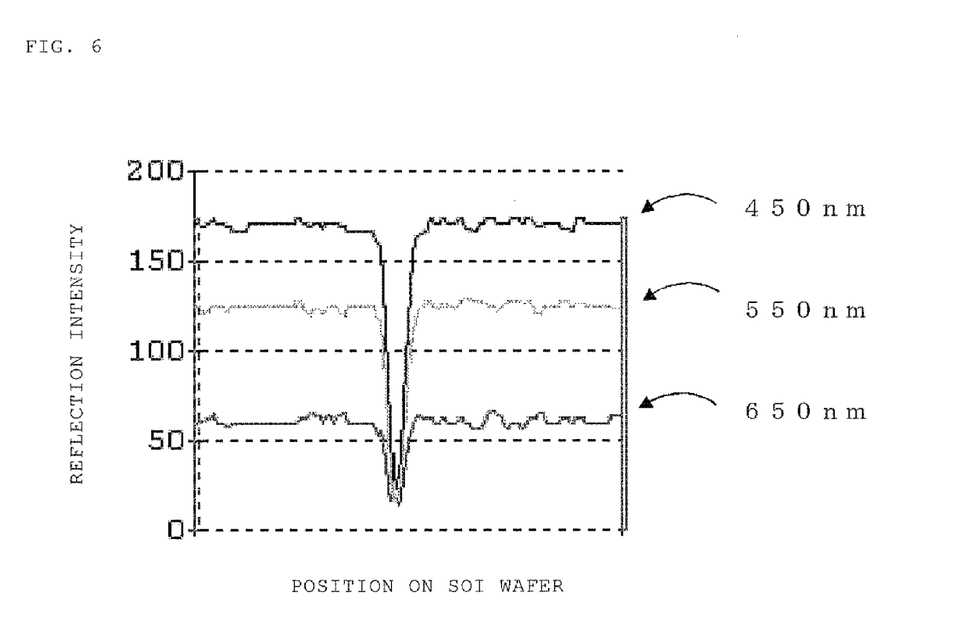
FIG. 6 is a graph showing another example of the reflection intensity of the detected reflected-light.

Moreover, FIG. 6 shows the result of experiment in which the reflection intensity of the reflected-light was measured when three types of light each having one of three wavelengths (450 nm, 550 nm, and 650 nm) were irradiated to an area of the SOI wafer actually having extraneous substances and not having the defects caused by the change in the film thickness of the SOI layer, as with the above-described experiment.

As shown in FIG. 6, the place of the downward peak is observed in cases of every wavelength. The extraneous substances were actually present at these places. That is, the place of the peak generated by the decrease in reflection intensity is observed at the position of the extraneous substance, and therefore the defect caused by the change in the film thickness of the SOI layer and the extraneous substance can be clearly distinguished to find the defect.

Figure 7:
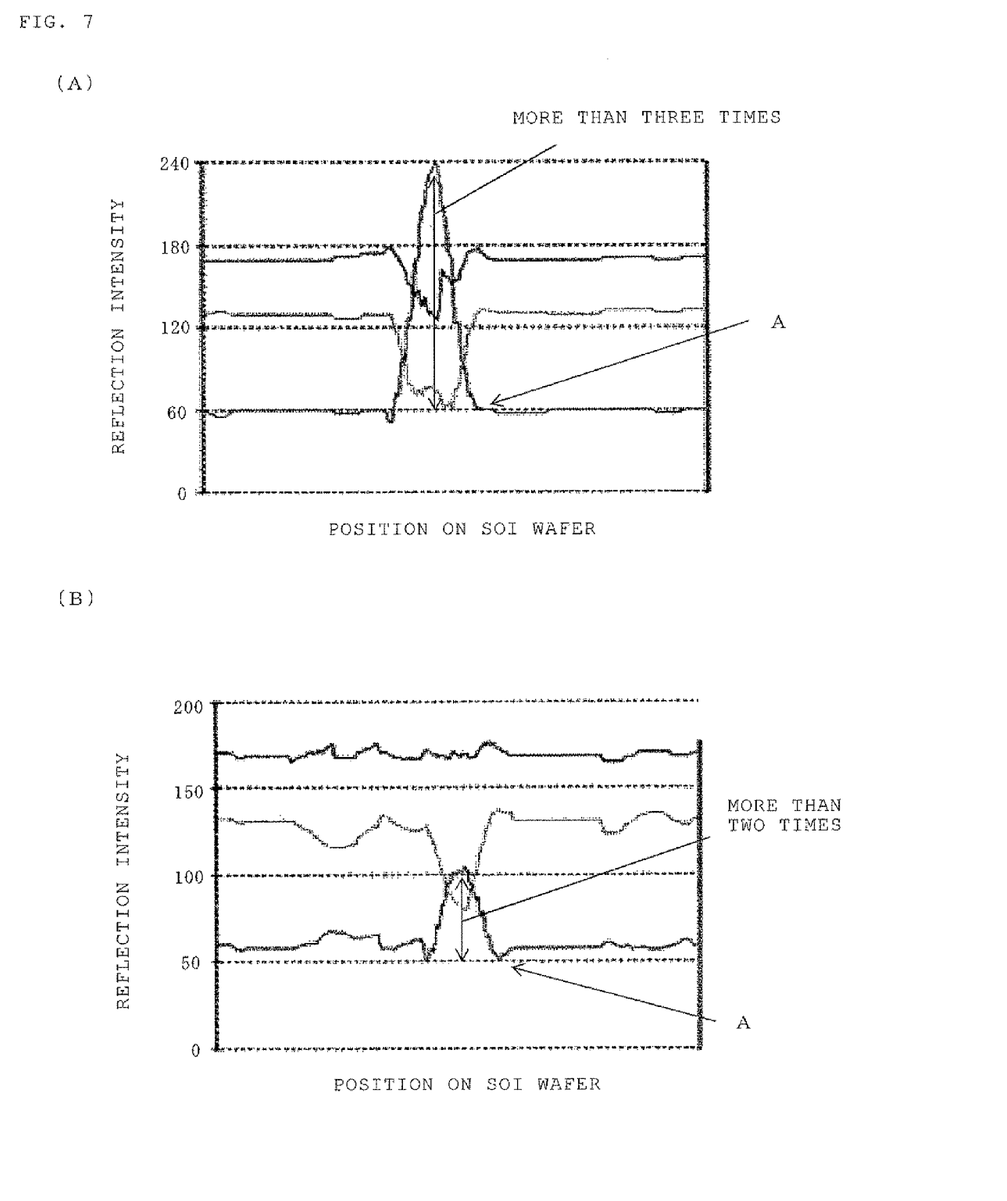
FIG. 7 includes views for explaining an example of setting the threshold value of the reflection intensity when the defects are found on the basis of the reflection intensity of the detected reflected-light, in which (A) shows the case of setting the threshold value at more than three times larger than the value of the place without the peak, and (B) shows the case of setting the threshold value at more than two times larger than the value of the place without the peak.

Here, when the defect is found, the threshold value of the reflection intensity can be set, and only the place of the peak where a value of the reflection intensity is equal to or more than a predetermined value is found as the defect. For example, as shown in FIG. 7 at (A) and (B), the threshold value can be set by using a ratio of the reflection intensity between places without the peak (A in FIG. 7 at (A) and (B)) and with the peak. FIG. 7 at (A) shows an example of the case where the defect can be found when the reflection intensity of the place of the peak generated by the increase in reflection intensity is three times larger than that of the place without the peak. FIG. 7 at (B) shows an example of the case where the defect can be found when the reflection intensity of the place of the peak generated by the increase in reflection intensity is two times larger than that of the place without the peak.

The above-described inspection method of an SOI wafer according to the present invention enables the defects caused by the change in the film thickness of the SOI layer on the SOI wafer surface to be found at high sensitivity and at low cost, without the influence of noise due to the extraneous substance present on the SOI layer. In addition to this, as described above, the defect caused by the change in the film thickness of the SOI layer and the extraneous substance can be clearly distinguished to find the defect by a direction of the peak of the reflection intensity of the reflected-light, and thereby only the defects caused by the change in the film thickness of the SOI layer can be selectively detected.

Figure 8:
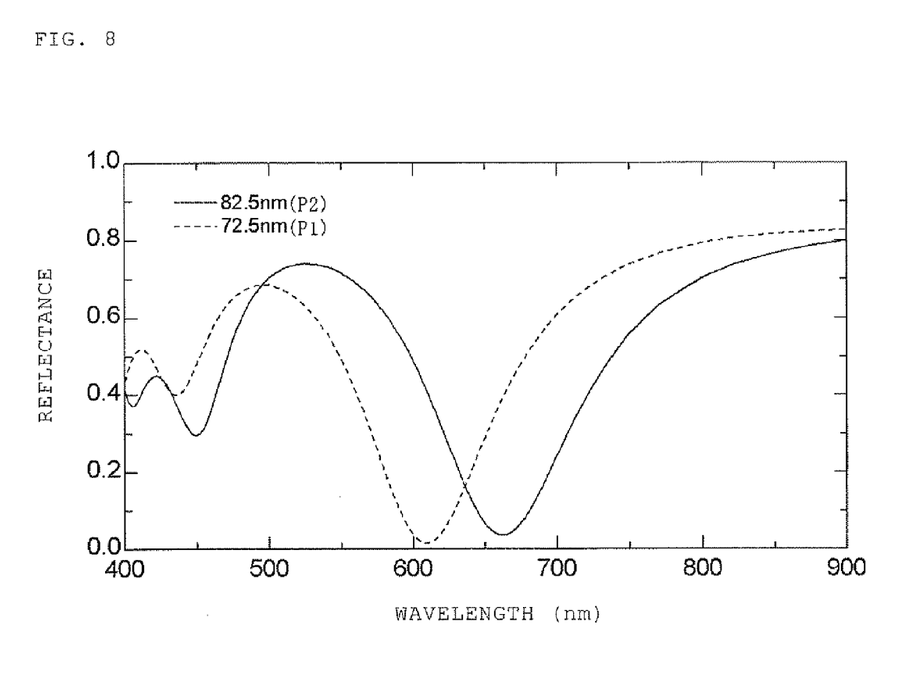
FIG. 8 is a graph showing another example of the calculated profiles P1 and P2.
Figure 9:
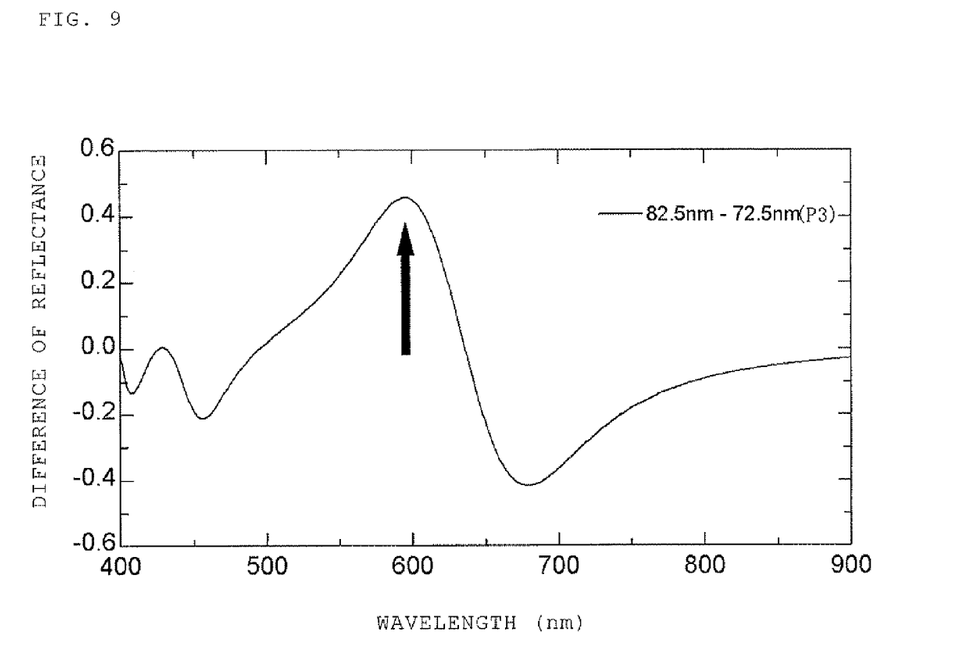
FIG. 9 is a graph showing another example of the calculated profile P3.

In case of finding the defects caused by the change due to the decrease in the film thickness of the SOI layer, as shown in FIG. 2, the profile P2 can be calculated in such a manner that the profile P2 of the SOI wafer having a film thickness of the SOI layer thinner by a thickness t is calculated. In case of finding the defects caused by the change due to the increase in the film thickness of the SOI layer, as shown in FIG. 8, the profile P2 can be calculated in such a manner that the profile P2 of the SOI wafer having a film thickness of the SOI layer thicker by a thickness t is calculated. FIG. 8 shows an example of the profile P1 of the SOI wafer to be inspected and the profile P2 of an SOI wafer having a film thickness of the SOI layer thicker than that of the SOI wafer to be inspected by 10 nm. FIG. 9 shows an example of the calculated profile P3 of the difference between the profiles P1 and P2 in this case. As shown in FIG. 9, some places showing the increasing peaks are observed in the profile P3 as with FIG. 3, and the place shown by an arrow is the maximum peak wavelength $\lambda_M$.

By calculating the profile P2 in this manner, the inspection can be performed by selecting the wavelength or wavelength band suitable for each of the defects caused by the changes due to the increase and the changes due to the decrease in the film thickness of the SOI layer. As a result, the defects can be found more surely at high sensitivity, and the defects caused by the changes due to the increase and decrease can be separately found.

Moreover, the predetermined thickness t is preferably set on the basis of film thickness uniformity of the SOI wafer to be inspected.

In this manner, when the predetermined thickness t is set on the basis of film thickness uniformity of the SOI wafer to be inspected, the inspection can be performed by selecting an appropriate wavelength or wavelength band on the basis of the film thickness uniformity, and it can be suppressed that the noise due to an nonuniform film thickness affects the inspection. The influence by the noise is, for example, that the noise, which does not show the defect, is mistakenly detected as the defect in the event that the predetermined thickness t is set at a small value against the SOI wafer having low film thickness uniformity. The defects caused by the change in the film thickness of the SOI layer can be thereby found more surely at high sensitivity.

Specifically, SOI wafers manufactured by, for example, the ion implantation delamination method (also called as the SMART-CUT method (registered trademark)) have the SOI layer having a film thickness uniformity in a wafer plane of ±3 nm or less. In this case, the predetermined thickness for decrease may be set at approximately 5 to 20 nm.

Moreover, in case of calculating the profile P2 of the SOI wafer having a film thickness of the SOI layer thinner by the predetermined thickness t in the step (B in FIG. 1) of calculating the profile P2, the wavelength $\lambda$ or wavelength band can be selected in a range of $\lambda_M-20$ [nm] to $\lambda_M+100$ [nm], in a subsequent step (C in FIG. 1), and in case of calculating the profile P2 of the SOI wafer having a film thickness of the SOI layer thicker by the predetermined thickness t in the step of calculating the profile P2, the wavelength $\lambda$ or wavelength band can be selected in a range of $\lambda_M-100$ [nm] to 4+20 [nm].

By calculating the profile P2 in this manner, it is possible to select the wavelength $\lambda$ or wavelength band that enables the inspection to be performed more surely at high sensitivity according to the profile P2. For example, in case of calculating the profile P2 of the SOI wafer having a film thickness of the SOI layer thinner by the predetermined thickness t as shown in FIG. 2, the profile P3 calculated in a subsequent step is shown in FIG. 3. As is obvious from FIG. 3, since an area where the reflection intensity becomes large continues extending in a longer wavelength side than $\lambda_M$, a wide wavelength range is more advantageous to integrated intensity. Moreover, since an area where the reflection intensity is reversed appears rapidly in a shorter wavelength side than $\lambda_M$, the wavelength range needs to be narrow. When the wavelength $\lambda$ or wavelength band is set in the above-described manner considering these, the defects can be found more surely at high sensitivity.

Moreover, in case of calculating the profile P2 of the SOI wafer having a film thickness of the SOI layer thicker by the predetermined thickness t as shown in FIG. 8, the profile P3 shows the content opposite to the above-described case of the film thickness thinner by the predetermined thickness t as show in FIG. 9, the wavelength range in a longer wavelength side than $\lambda_M$ can be set at a narrow range, and the wavelength range in a shorter wavelength side than $\lambda_M$ can be set at a wide range.

Figure 11:
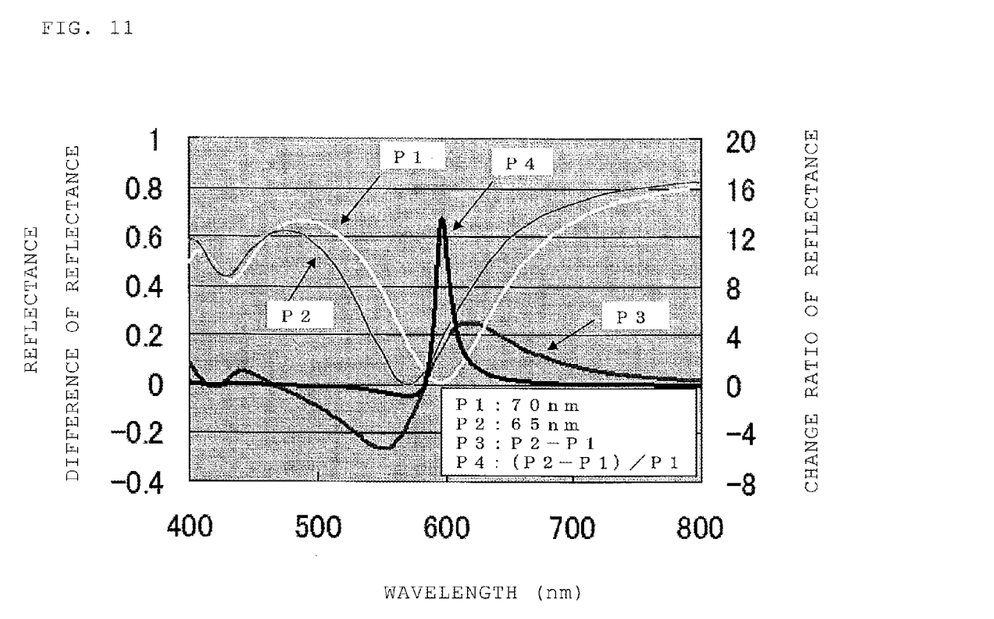
FIG. 11 is a graph showing another example of the calculated profiles P1, P2, P3, and P4.

Hereinbefore, there is mainly described in detail the case of selecting the wavelength $\lambda$ or the wavelength band by using the difference P3 between the profiles P1 and P2. The wavelength $\lambda$ or the wavelength band can be also selected by using the change ratio 94 of the profiles P1 and P2. FIG. 11 shows another example of the profiles P1, P2, P3, and P4, in which the film thickness S of the SOI layer of the SOI wafer to be inspected is 70 nm, and the thickness B of the buried insulator layer thereof is 145 nm. As shown in FIG. 11, the place showing the maximum peak wavelength $\lambda_M$ is observed in P4, and the wavelength $\lambda$ or the wavelength band can be selected by the same method as the case of P3 as described above.

Hereinafter, the present invention will be explained in more detail with reference to Example and Comparative Example, but the present invention is not restricted thereto.

Example

The defects caused by the change in the film thickness of the SOI layer were found on the basis of the inspection method of an SOI wafer according to the present invention as shown in FIG. 1. The film thickness S of the SOI layer of the SOI wafer to be inspected was 72.5 nm, and the thickness B of the buried insulator layer thereof was 145 nm. The profile P1 of the SOI wafer to be inspected was calculated, and the profile P2 of an SOI wafer having a 62.5 nm film thickness of the SOI layer thinner than that of the SOI wafer to be inspected by a predetermined thickness of 10 nm was calculated. Next, the profile P3 of the difference between the profiles P1 and P2 was calculated, and a wavelength band of 600 to 720 nm was selected on the basis of P3. Next, visible light having the selected wavelength band was irradiated to the SOI wafer to detect the reflected-light from the SOI wafer. The places of the peaks generated by the increase in reflection intensity of the detected reflected-light were found as the defects caused by the change in the film thickness of the SOI layer.

Figure 10:
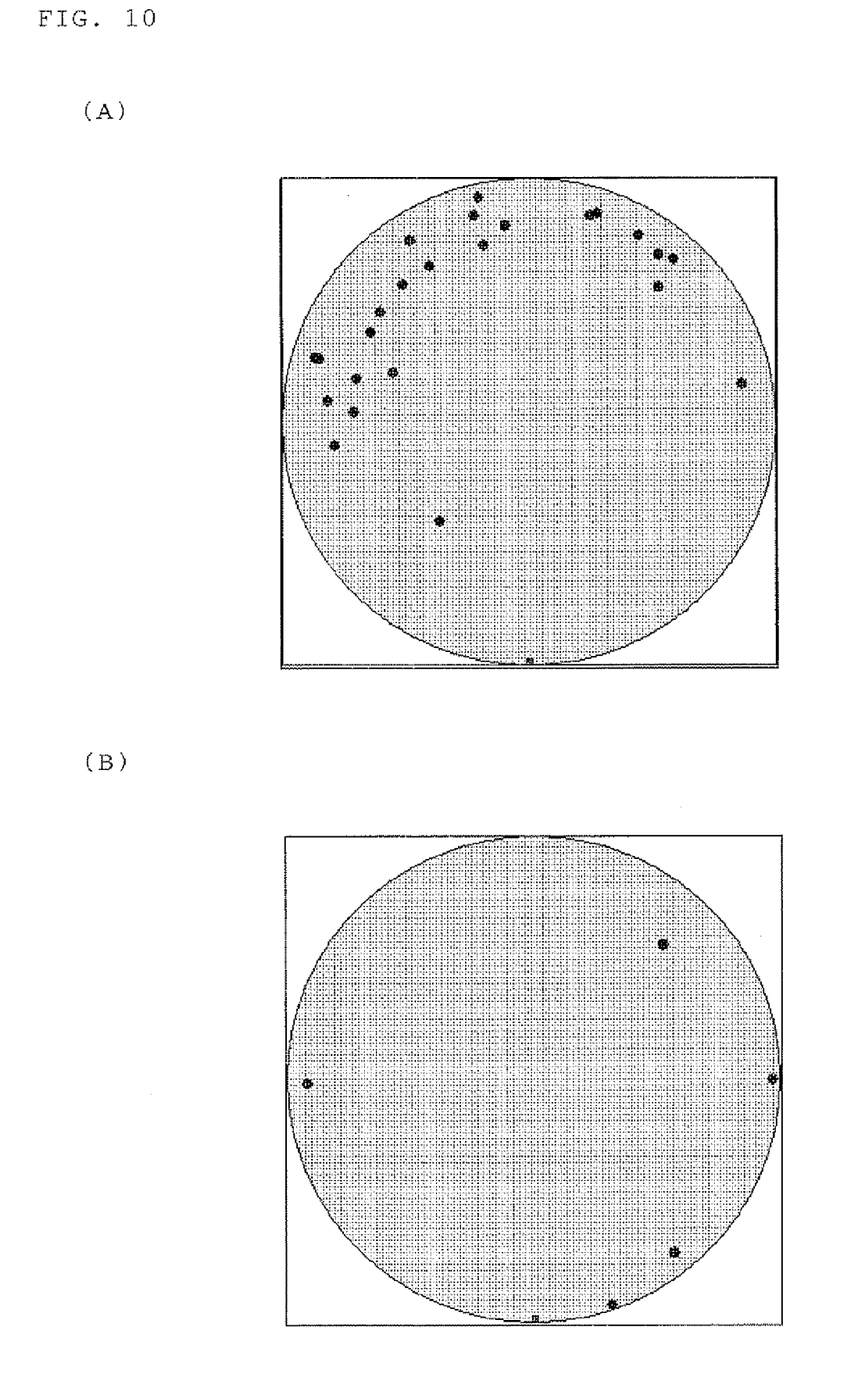
FIG. 10 includes views showing the inspection results of the defects of the SOI wafer in Example and Comparative Example, in which (A) shows the result of Example, and (B) shows the result of Comparative Example.

As a result, as shown in FIG. 10 at (A), 23 defects caused by the change in the film thickness of the SOI layer were found. As a result of investigating the positions of the found defects by a microscope, it was confirmed that all of the 23 defects found were actually present.

As described above, it was confirmed that the inspection method of an SOI wafer according to the present invention enables the defects caused by the change in the film thickness of the SOI layer on the surface of the SOI wafer to be found at high sensitivity and at low cost, without the influence of noise due to the extraneous substance present on the SOI layer.

Comparative Example

The defects on the surface of the same SOI wafer as Example was inspected on the basis of a conventional inspection method of an SOI wafer using the laser scattering method. Laser light having a single wavelength of 355 nm was irradiated to the SOI wafer with an apparatus of SP2 made by KLA-Tencor Co., Ltd. and the defects were found by setting a condition for finding a particle of 100 nm or more and by receiving the scattered light from the SOI wafer.

As a result, as shown in FIG. 10 at (B), 5 particles were found. Furthermore, it was confirmed that all of the positions of the 5 particles were different from that of the defects caused by the change in the film thickness of the SOI layer, found in Example.

As described above, the inspection method of an SOI wafer according to the present invention enables the defects, which are caused by the change in the film thickness of the SOI layer and cannot be found by the conventional inspection method of an SOI wafer using the laser scattering method, to be found.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. An inspection method of an SOI wafer including, using an optical inspection apparatus having a light source for irradiating light having a wavelength band of a visible light wavelength or more to irradiate the light from the light source to a surface of the SOI wafer having an SOI layer formed on a buried insulator layer, and detecting reflected-light from the SOI wafer to find defects caused by changes due to an increase and a decrease in a film thickness of the SOI layer on the surface of the SOI wafer, the method comprising at least the steps of:

calculating a profile P1 showing wavelength dependency of reflectance with respect to the light having a wavelength band of a visible light wavelength or more, in the SOI wafer to be inspected;

calculating a profile P2 showing wavelength dependency of reflectance with respect to the light having a wavelength band of a visible light wavelength or more, in an SOI wafer having a film thickness of the SOI layer thicker or thinner than that of the SOI wafer to be inspected by a predetermined thickness t [nm];

calculating a profile P3 (=P2−P1) of a difference between the calculated profiles P1 and P2, or a profile P4 (=(P2−P1)/P1) of a change ratio of the calculated profiles P1 and P2, to select a wavelength λ or a wavelength band in close vicinity of a maximum peak wavelength $\lambda_M$ within the calculated profiles P3 or P4;

irradiating light having the selected wavelength λ or wavelength band to the surface of the SOI wafer to be inspected, to detect the reflected-light from the SOI wafer; and finding a place of a peak generated by an increase in reflection intensity of the detected reflected-light, as the defect caused by the change in the film thickness of the SOI layer on the surface of the SOI wafer.

2. The inspection method of an SOI wafer according to claim 1, wherein the predetermined thickness t is set in a range of 5 to 20 nm.

3. The inspection method of an SOI wafer according to claim 1, wherein, in case of calculating the profile P2 of the SOI wafer having a film thickness of the SOI layer thinner by the predetermined thickness t in the step of calculating the profile P2, the wavelength λ or wavelength band is selected in a range of $\lambda_M$−20 [nm] to $\lambda_M$+100 [nm], and in case of calculating the profile P2 of the SOI wafer having a film thickness of the SOI layer thicker by the predetermined thickness t in the step of calculating the profile P2, the wavelength λ or wavelength band is selected in a range of $\lambda_M$−100 [nm] to $\lambda_M$+20 [nm].

4. The inspection method of an SOI wafer according to claim 1, wherein the predetermined thickness t is set on the basis of film thickness uniformity of the SOI wafer to be inspected.

5. The inspection method of an SOI wafer according to claim 4, wherein the predetermined thickness t is set m a range of 5 to 20 nm.

6. The inspection method of an SOI wafer according to claim 1, wherein a threshold value of the reflection intensity of the detected reflected-light is set, and the defects having the reflection intensity equal to or more than the threshold value are selectively found.

7. The inspection method of an SOI wafer according to claim 6, wherein the predetermined thickness t is set m a range of 5 to 20 nm.

8. The inspection method of an SOI wafer according to claim 6, wherein the predetermined thickness t is set on the basis of film thickness uniformity of the SOI wafer to be inspected.

9. The inspection method of an SOI wafer according to claim 8, wherein the predetermined thickness t is set m a range of 5 to 20 nm.

10. The inspection method of an SOI wafer according to claim 1, wherein, in case of finding the defects caused by the change due to the decrease in the film thickness of the SOI layer, the profile P2 of the SOI wafer having a film thickness of the SOI layer thinner by a thickness t is calculated in the step of calculating the profile P2, and in case of finding the defects caused by the change due to the increase in the film thickness of the SOI layer, the profile P2 of the SOI wafer having a film thickness of the SOI layer thicker by a thickness t is calculated in the step of calculating the profile P2.

11. The inspection method of an SOI wafer according to claim 10, wherein the predetermined thickness t is set in a range of 5 to 20 nm.

12. The inspection method of an SOI wafer according to claim 10, wherein the predetermined thickness t is set on the basis of film thickness uniformity of the SOI wafer to be inspected.

13. The inspection method of an SOI wafer according to claim 12, wherein the predetermined thickness t is set m a range of 5 to 20 nm.

14. The inspection method of an SOI wafer according to claim 10, wherein a threshold value of the reflection intensity of the detected reflected-light is set, and the defects having the reflection intensity equal to or more than the threshold value are selectively found.

15. The inspection method of an SOI wafer according to claim 14, wherein the predetermined thickness t is set m a range of 5 to 20 nm.

16. The inspection method of an SOI wafer according to claim 14, wherein the predetermined thickness t is set on the basis of film thickness uniformity of the SOI wafer to be inspected.

17. The inspection method of an SOI wafer according to claim 16, wherein the predetermined thickness t is set m a range of 5 to 20 nm.

18. The inspection method of an SOI wafer according to claim 17, wherein, in case of calculating the profile P2 of the SOI wafer having a film thickness of the SOI layer thinner by the predetermined thickness t in the step of calculating the profile P2, the wavelength $\lambda$ or wavelength band is selected in a range of $\lambda_M-20$ [nm] to $\lambda_M+100$ [nm], and in case of calculating the profile P2 of the SOI wafer having a film thickness of the SOI layer thicker by the predetermined thickness t in the step of calculating the profile P2, the wavelength $\lambda$ or wavelength band is selected in a range of $\lambda_M-100$ [nm] to $\lambda_M+20$ [nm].

* * * * *